US010040062B2

(12) United States Patent
Beebe et al.

(10) Patent No.: US 10,040,062 B2
(45) Date of Patent: Aug. 7, 2018

(54) DEVICE AND METHOD FOR TRANSFERRING A TARGET BETWEEN LOCATIONS

(71) Applicant: Wisconsin Alumni Research Foundation, Madison, WI (US)

(72) Inventors: David J. Beebe, Monona, WI (US); Ben P. Casavant, Madison, WI (US); David J. Guckenberger, Oconomowoc, WI (US); Scott M. Berry, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 183 days.

(21) Appl. No.: 14/154,695

(22) Filed: Jan. 14, 2014

(65) Prior Publication Data

US 2015/0196907 A1 Jul. 16, 2015

(51) Int. Cl.
*B01L 3/00* (2006.01)
*C12Q 1/68* (2018.01)
(Continued)

(52) U.S. Cl.
CPC ........... *B01L 3/0268* (2013.01); *B01L 3/5088* (2013.01); *B01L 3/50825* (2013.01); *B01L 3/563* (2013.01);
(Continued)

(58) Field of Classification Search
CPC ...... B01L 3/5023; B01L 99/00; B01L 3/0268; B01L 3/50825; B01L 3/5088; B01L 3/563
(Continued)

(56) References Cited

U.S. PATENT DOCUMENTS 4,292,920 A * 10/1981 Smith .................. B03C 1/0332 118/425
4,987,508 A 1/1991 Smith
(Continued)

FOREIGN PATENT DOCUMENTS

WO 200671770 7/2006
WO 2007110779 10/2007

OTHER PUBLICATIONS

U.S. Appl. No. 60/638,177, filed Dec. 21, 2005, Collier et al.
(Continued)

*Primary Examiner* — Jill A Warden
*Assistant Examiner* — Jacqueline Brazin
(74) *Attorney, Agent, or Firm* — Boyle Fredrickson, S.C.

(57) ABSTRACT

A device and method are proved for transferring a target from a first location to a second location. The target is bound to solid phase substrate to form a target bound solid phase substrate. The device includes transfer surface for receiving the target bound solid phase substrate thereon for transfer. The transfer surface movable between a first position wherein the transfer surface is aligned with the first location and spaced therefrom by a distance and a second position wherein the transfer surface is aligned with the second location. An alignment structure aligns the transfer surface with respect to the second location, with the transfer surface in the second position. A force is movable between an attraction position wherein the target bound solid phase substrate are drawn toward the transfer surface and a discharge position wherein the target bound solid phase substrate are free of the force.

21 Claims, 10 Drawing Sheets

(51) Int. Cl.
*B01L 99/00* (2010.01)
*B01L 3/02* (2006.01)

(52) U.S. Cl.
CPC . *B01L 2200/025* (2013.01); *B01L 2200/0657* (2013.01); *B01L 2200/0668* (2013.01); *B01L 2300/042* (2013.01); *B01L 2400/021* (2013.01); *B01L 2400/043* (2013.01)

(58) Field of Classification Search
USPC .......................................... 422/538; 436/526
See application file for complete search history.

(56) References Cited

U.S. PATENT DOCUMENTS

| | | | | |
|---|---|---|---|---|
| 5,279,936 | A | 1/1994 | Vorpahl | |
| 5,567,326 | A * | 10/1996 | Ekenberg | B03C 1/0332 210/222 |
| 6,117,398 | A | 9/2000 | Bienhaus et al. | |
| 7,820,454 | B2 | 10/2010 | Su et al. | |
| 8,017,340 | B2 | 9/2011 | Collier et al. | |
| 8,048,633 | B2 | 11/2011 | Collier et al. | |
| 8,124,024 | B2 * | 2/2012 | Ching | B01F 11/0071 137/15.01 |
| 8,292,083 | B2 * | 10/2012 | Varghese | B03C 1/0332 209/215 |
| 8,304,188 | B2 | 11/2012 | Kelso et al. | |
| 2004/0224380 | A1 | 11/2004 | Chou et al. | |
| 2005/0112601 | A1 | 5/2005 | Hassibi et al. | |
| 2005/0208548 | A1 | 9/2005 | Block et al. | |
| 2005/0227349 | A1 | 10/2005 | Kim et al. | |
| 2006/0024824 | A1 | 2/2006 | Woodside et al. | |
| 2006/0118494 | A1 * | 6/2006 | Rundt | B03C 1/284 210/695 |
| 2007/0042396 | A1 | 2/2007 | Park et al. | |
| 2008/0124779 | A1 | 5/2008 | Oh et al. | |
| 2008/0160634 | A1 | 7/2008 | Su et al. | |
| 2008/0226500 | A1 | 9/2008 | Shikida et al. | |
| 2009/0053799 | A1 | 2/2009 | Chang-Yen et al. | |
| 2009/0078614 | A1 * | 3/2009 | Varghese | B03C 1/0332 209/39 |
| 2009/0191594 | A1 | 7/2009 | Ohashi | |
| 2009/0246782 | A1 | 10/2009 | Kelso et al. | |
| 2009/0325192 | A1 | 12/2009 | Kirakossian et al. | |
| 2010/0213133 | A1 | 8/2010 | Kasaini | |
| 2010/0273142 | A1 * | 10/2010 | Prins | B01L 3/502738 435/4 |
| 2010/0291666 | A1 | 11/2010 | Collier et al. | |
| 2011/0000930 | A1 * | 1/2011 | Logel | B65D 43/162 220/849 |
| 2011/0053289 | A1 | 3/2011 | Lowe et al. | |
| 2011/0079582 | A1 | 4/2011 | Yonesu et al. | |
| 2011/0091989 | A1 * | 4/2011 | Sista | B01L 3/502761 436/174 |
| 2011/0136250 | A1 | 6/2011 | Ran et al. | |
| 2012/0094275 | A1 | 4/2012 | Rao et al. | |
| 2012/0145390 | A1 | 6/2012 | Parse et al. | |
| 2012/0178096 | A1 | 7/2012 | Beebe et al. | |
| 2012/0190037 | A1 * | 7/2012 | Durin | G01N 33/56911 435/6.15 |
| 2013/0214156 | A1 | 8/2013 | Kneedler et al. | |
| 2015/0196905 | A1 * | 7/2015 | Pinard | B01L 3/5021 422/548 |
| 2016/0137974 | A1 * | 5/2016 | Souza | C12M 23/10 435/173.1 |

OTHER PUBLICATIONS

"Development of an enzymatic reaction device using magnetic bead-cluster handling", Shikida et al, J. Micromech. Microeng. 16 (2006) 1875-1883.
"Controlled microfluidic interfaces", Atencia et al, Nature, vol. 437, Sep. 29, 2005, 648-655.
"Using wettability and interfacial tension to handle droplets of magnetic beads in a micro-chemical-analysis system", Shikida et al, Sensors and Actuators B 113 (2006) 563-569.
"Droplet-based gene expression analysis using a device with magnetic force-based-droplet-handling system", Okochi et al, Journal of Bioscience and Bioengineering, vol. 109, No. 2, 2010, 193-197.
"On-chip polymerase chain reaction microdevice employing a magnetic droplet-manipulation system", Tsuchiya et at, Sensors and Actuators B 130 (2008) 583-588.
"A novel Real Time micro PCR based Point-of-Care device for *Salmonella* detection in human clinical samples", Verdoy et al, Biosensors and Bioelectronics 332 (2012) 259-265.
"Forced motion of a probe particle near the colloidal glass transition", Habdas et al, Europhys. Lett., 67(3). pp. 477-583 (2004).
"One-step purification of nucleic acid for gene expression analysis via immiscible filtration assisted by surface tension (IFAST)", Berry et al., Lab on a Chip, vol. 11, No. 10, pp. 1747-1753 (2011).
"Facile and rapid DNA extraction and purification from food matrices using IFAST (immiscible filtration assisted by surface tension)", Strotman et al., Analyst, vol. 137, No. 17, pp. 4023-4028 (2012).
"Streamlining immunoassays with immiscible filtrations assisted by surface tension", Berry et al., Analytical Chemistry, vol. 84, No. 13, pp. 5518-5523 (2012).
"Immiscible phase nucleic acid purification eliminates PCR inhibitors with a single pass of paramagnetic particles through a hydrophobic liquid", Sur et al., The Journal of Molecular Diagnostics, vol. 12, No. 5, pp. 620-628 (2010).
"Removal of malaria-infected red blood cells using magnetic cell separators: A computational study", Kim et al., Applied Mathematics and Computation, vol. 218, No. 12, pp. 6841-6850 (2012).
"Development of a Low-Resource RNA Extraction Cassette Based on Surface Tension Valves", Bordelon et al., Appl. Mater. Interfaces 2011, 3, 2161-2168.
"One-Step Isolation of Transitory Protein Complex With IFast", Berry et al., The 16th International Conference on Miniaturized Systems for Chemistry and Life Sciences, 2012 Okinawa Japan, pp. 163-165.

* cited by examiner

DEVICE AND METHOD FOR TRANSFERRING A TARGET BETWEEN LOCATIONS

REFERENCE TO GOVERNMENT GRANT

This invention was made with government support under W81XWH-09-1-0192 awarded by the ARMY/MRMC and CA160344 awarded by the National Institutes of Health. The government has certain rights in the invention.

FIELD OF THE INVENTION

The present invention relates generally to the transfer of a target, such as an analyte, between locations, and in particular, to a device and a method for transferring the target from a first location, e.g. a drop, a test tube, a well of a microfluidic device, a microwell of a conventional well plate or the like, to a second location, e.g. a test tube, a well of a microfluidic device, a microwell of a conventional well plate or the like, to enable further downstream processing of the target.

BACKGROUND AND SUMMARY OF THE INVENTION

As is known, polymerase chain reaction (PCR) is a biochemical technology wherein a specific region of a Deoxyribonucleic acid (DNA) strand (the DNA target) is amplified across several orders of magnitude to generate copies of a particular DNA sequence. PCR has become a common and indispensable technique used in medical and biological research labs for a variety of applications. However, the methods of isolating/preparing samples of the DNA target for PCR that are commonly in use are both time consuming and tedious.

Recent technological developments have accelerated the purification process. By way of example. Beebe et al., U.S. Patent Application Publication No. 2011/0213133, incorporated by reference herein in its entirety, discloses a device and a method for facilitating extraction of a fraction such as a DNA target from a biological sample. The biological sample includes non-desired material and a fraction-bound solid phase substrate. The device includes an input zone for receiving the biological sample therein and a phase-gate zone for receiving an isolation buffer therein. An output zone receives a reagent therein. A force is movable between a first position adjacent the input zone and a second position adjacent the output zone. The force urges the fraction-bound solid phase substrate from the input zone, through the phase-gate zone and into the output zone.

While functional for its intended purpose, the Beebe et al., '133 publication does not contemplate a specific structure for integrating the device disclosed therein with instruments, such as PCR machines, light cyclers, or thermocyclers, for downstream analysis. Current methods of integration involve transferring the DNA target via pipetting to a tube, strip tubes, or a well plate which is compatible with the plethora of instruments available for downstream analysis and processing. It can be appreciated that it would be highly desirable to provide a device that directly integrates with existing tubes, strip tubes, and well plates and that streamlines the process for transferring the DNA target from the device disclosed in the Beebe et al., '133 publication (as well as, similar type devices) to the various instruments currently available for downstream analysis.

Therefore, it is a primary object and feature of the present invention to provide a device and a method for transferring a target between locations.

It is a further object and feature of the present invention to provide a device and a method for transferring a target that allows for the simple integration of a microfluidic device with instruments, such as PCR machines, light cyclers, mass spectrometers, spectrophotomers, or thermocyclers, for downstream analysis.

It is a still a further object and feature of the present invention to provide a device and a method for transferring a target between locations which is simple to use and inexpensive to manufacture.

In accordance with the present invention, a device is provided for transferring a target from a first location to a second location. The target is bound to solid phase substrate to form a target bound solid phase substrate. The device includes a transfer surface having a first region for receiving the target bound solid phase substrate thereon for transfer. The transfer surface is movable between a first position wherein the transfer surface is aligned with the first location and spaced therefrom by a distance and a second position wherein the transfer surface is aligned with the second location. An alignment structure aligns the transfer surface with respect to the second fluid with the transfer surface in the second location. A force is movable between an attraction position wherein the target bound solid phase substrate are drawn toward the first region of the transfer surface and a discharge position wherein the target bound solid phase substrate are freed of the force. The force may be magnetic.

It is contemplated for a first fluid to be received in a sample container at the first location. The inner surface of the sample container can be hydrophobic which causes the first fluid in the sample container to have a non-concave meniscus. Alternatively, an insert may be receivable in the sample container along the inner surface thereof. The insert causes the first fluid in the sample container to have a non-concave meniscus. A second fluid may received in a receptacle at the second location.

The alignment structure includes a plate. The transfer surface extends along a first side of the plate and overlaps the upper edge of the receptacle with the transfer surface in the second position. In addition, the alignment structure may include a wall depending from the transfer surface. The wall may have an inner surface that defines the first region of the transfer surface and an outer surface engageable with the inner surface of the receptacle with the transfer surface in the second position. The alignment structure may also include a second wall depending from the transfer surface. The second wall has an inner surface engageable with the outer surface of the receptacle with the transfer surface in the second position and an outer surface. Alternatively, an inner surface of the wall depending from the transfer surface may be engageable with the outer surface of the receptacle with the transfer surface in the second position and an outer surface. The first region of the transfer surface may include a pinning element extending about the outer periphery thereof. The pinning element retains transfer fluid in the first region of the transfer surface. The plate includes an upper surface on a second side thereof. The force is adjacent the upper surface of the plate with the force in the attraction position.

In an alternate embodiment, the alignment structure may include a plate and a transfer element depending a first side thereof. The transfer element terminates at the transfer surface and has an outer surface engageable with the inner surface of the receptacle with the transfer surface in the second position. In addition, the first side of the plate is engageable with the upper edge of the receptacle with the transfer surface in the second position.

An intermediate fluid may be disposed between the transfer surface and the first location. In such arrangement, the target bound solid phase substrate passes through the intermediate fluid as the target bound solid phase substrate are drawn from the first location to the first region of the transfer surface.

In accordance with a further aspect of the present invention, a device is provided for transferring a target from a first fluid at a first location to a second location. The target is bound to solid phase substrate to form target bound solid phase substrate. The device includes a means for forming a non-concave meniscus with the first fluid. A transfer region receives the target bound solid phase substrate for transfer. The transfer region is movable between a first position wherein the transfer region is aligned with the meniscus of the first fluid and spaced therefrom and a second position wherein the transfer region is aligned with the second location. An alignment structure aligns the transfer region with respect to the receptacle with the transfer region in the second position. A force is movable between an attraction position wherein the target bound solid phase substrate are drawn toward the first region of the transfer surface and a discharge position wherein the target bound solid phase substrate are freed of the force.

The first fluid may be received in a sample container. The forming means may include an inner surface of the sample container being hydrophobic, thereby causing the first fluid in the sample container to have the non-concave meniscus. Alternatively, forming means may including an insert receivable in the sample container along the inner surface thereof. The insert causes the first fluid in the sample container to have the non-concave meniscus.

An intermediate fluid may be disposed between the transfer region and the first fluid. The target bound solid phase substrate passes through the intermediate fluid as the target bound solid phase substrate are drawn from the first fluid to the transfer region.

The alignment structure includes a plate and receptacle is provide at the second location. The transfer region extends along a first side of the plate and the plate overlaps the upper edge of the receptacle with the transfer region in the second position. The alignment structure may also include a wall depending from the transfer first side of the plate. The wall is engageable with the receptacle with the transfer region in the second position. Transfer fluid may be provided at the transfer region and a pinning element may extend about the outer periphery of the transfer region. The pinning element retains the transfer fluid in the transfer region.

In accordance with a further aspect of the present invention, a method is provided for transferring a target from a first fluid at a first location to a second location. The target is bound to solid phase substrate to form target bound solid phase substrate. The method includes the steps of forming a non-concave meniscus with the first fluid and drawing the target bound solid phase substrate from the first fluid into a transfer region of a transfer device. The transfer region is aligned with the second fluid. The target bound solid phase substrate is released and passes to the second location.

The step of forming the non-concave meniscus with the first fluid may include the additional steps of depositing the first fluid in a sample container and inserting an insert into the sample container, the insert causing the first fluid in the sample container to form the non-concave meniscus. Alternatively, the step of forming the non-concave meniscus with the first fluid may include the additional step of depositing the first fluid in a sample container having a hydrophobic inner surface. The hydrophobic inner surface causes the first fluid in the sample container to form the non-concave meniscus. It is contemplated to position an intermediate fluid between the first fluid and the transfer region, and pass the target bound solid phase substrate through the intermediate fluid as the target bound solid phase substrate are drawn from the first fluid to the transfer region.

BRIEF DESCRIPTION OF THE DRAWINGS

The drawings furnished herewith illustrate a preferred construction of the present invention in which the above aspects, advantages and features are clearly disclosed as well as others which will be readily understood from the following description of the illustrated embodiments.

In the drawings.

DETAILED DESCRIPTION OF THE DRAWINGS

Figure 1:
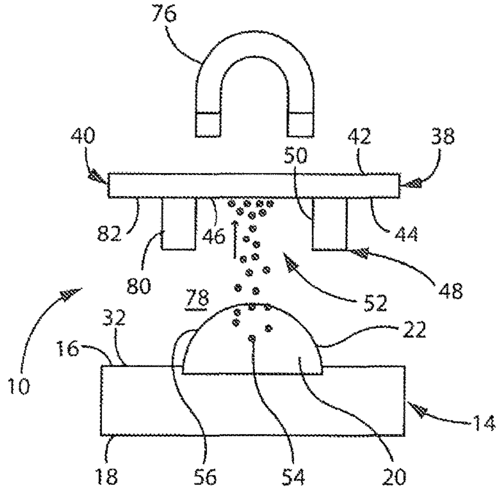
FIG. 1 a schematic, cross-sectional view of a first portion of a device in accordance with the present invention.
Figure 2:
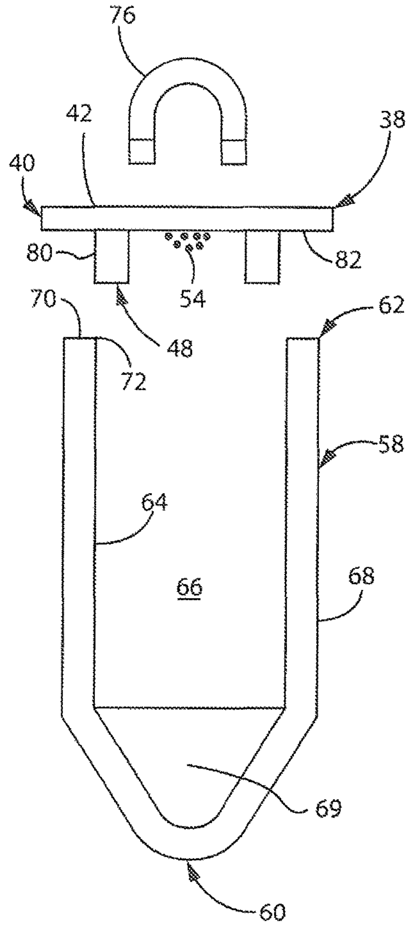
FIG. 2 an exploded, schematic, cross-sectional view of a second portion of the device of the present invention.
Figure 3:
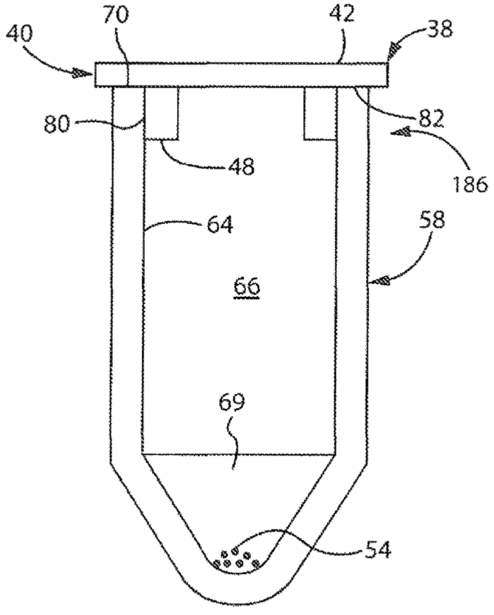
FIG. 3 is a schematic, cross-sectional view of the second portion of the device of the present invention.

Referring to FIGS. 1-3, a first embodiment device for transferring a targeted fraction, such as an analyte or the like, from a first location, such as a first fluid or a first surface to a second location such as a second fluid or a second surface in accordance with the present invention is generally designated by the reference numeral 10. In the depicted embodiment, device 10 includes lower plate 14 having upper and lower surfaces 16 and 18, respectively. Except as hereinafter described, upper surface 16 of lower plate 14 is hydrophobic. Upper surface 16 of lower plate 14 includes first region 20 defined by edge 22 such that first region 20 has a generally circular configuration. However, other configurations are contemplated as being within the scope of the present invention. It is intended for first region 20 to retain a selected first fluid thereon, as hereinafter described. As such, it is contemplated for first region 20 to be hydrophilic. Further, it is noted that the portion of upper surface 16 of lower plate 14 outside of first region 20 defines hydrophobic region 32 of upper surface 16 of lower plate 14.

Device 10 further includes transfer mechanism 38. Transfer mechanism 38 includes upper plate 40 having upper and, lower surfaces 42 and 44, respectively. Except as hereinafter described, lower surface 44 of upper plate 40 is hydrophobic. Lower surface 44 of upper plate 40 includes first region 46 defined by generally cylindrical sidewall 48 depending from lower surface 44 of upper plate 40 such that first region 46 has a generally circular configuration. As described, inner surface 50 of cylindrical sidewall 48 defines retention well 52, for reasons hereinafter described. It can be appreciated that other configurations of first region 46, cylindrical sidewall 48 and retention well 52 are contemplated as being within the scope of the present invention. By way of example, first region 46 may retain a selected fluid thereon and within retention well 52, as hereinafter described. As such, it is contemplated for first region 46 to be hydrophilic. It is further contemplated for inner surface 50 to be hydrophilic so as to facilitate the retention of the selected fluid in retention well 52.

It is intended to utilize device 10 to transfer a targeted fraction, such as an analyte, DNA, RNA, proteins, small molecules, nucleic acids, whole cells and/or the like, from a first fluid to a second fluid provided for in receptacle 58, such as a test tube or an individual well of a well plate. Referring to FIG. 2, receptacle 58 includes a first closed end 60 and second open end 62. Inner surface 64 of receptacle 58 defines chamber 66 for receiving second fluid 69 therein. Receptacle 58 is further defined by outer surface 68 and by upper edge 70, which extends between inner and outer surfaces 64 and 68, respectively, and which defines opening 72 in open end 62. Opening 72 allows for fluid communication with the interior of chamber 66 of receptacle 58.

In order to prepare the first fluid for extraction of the targeted fraction, an appropriate reagent is added to the first fluid and mixed such that the targeted fraction binds to a solid phase substrate in the reagent to form target bound solid phase substrate 54. It is contemplated for the solid phase substrate to be attracted to a corresponding force. For example, the solid phase substrate may be a paramagnetic material attracted to a corresponding magnetic field. Other non-magnetic mechanisms such as gravity, optical force, ultrasonic actuation or the like are contemplated as being within the scope of the present invention.

Once mixed with the reagent, drop 56 of the first fluid is deposited on first region 20 of lower plate 14, in any conventional matter such as by a micropipette or like. In order to facilitate the transfer of target bound solid phase substrate 54 from drop 56 to transfer mechanism 38, as hereinafter described, it is necessary for drop 56 to have a non-concave-shaped meniscus such that target bound solid phase substrate 54 cluster at the center or the apex of drop 56. By way of example, it is noted that drop 56 has a generally concave meniscus. Thereafter, transfer mechanism 38 is positioned such that retention well 52 is axially aligned with first region 20 of lower plate 14, and hence, with drop 56. Lower surface 44 of upper plate 40 may be spaced from drop 56 by air gap 78 or in engagement with an gap 78 without deviating from the scope of the present intention. A single magnet 76 is positioned adjacent upper surface 42 of upper plate 40. It is contemplated for magnet 76 to be axially movable between a first position wherein magnet 76 is adjacent to upper surface 42 of upper plate 40 and a second position wherein magnet 76 is axially spaced from upper surface 42 of upper plate 40, for reasons hereinafter described. With magnet 76 in the first position, as heretofore described, magnet 76 magnetically attracts target bound solid phase substrate 54 in drop 56 and draws target bound solid phase substrate 54 toward first region 46 of transfer mechanism 38. More specifically, the magnetic force generated by magnet 76 draws target bound solid phase substrate 54 from drop 56 through air gap 78 to first region 46. Any undesired (or unbound) material in drop 56 is retained therein by surface tension.

Once target bound solid phase substrate 54 is captured by transfer mechanism 38, it is contemplated that the hydrophilic nature of first region 46 of lower surface 44 of upper plate 40 of transfer mechanism 38 retain target bound solid phase substrate 54 thereon without the need for the magnetic force of magnet 76. As such, magnet 76 may be moved to the second position as transfer mechanism 38 is moved into a mating relationship with receptacle 58, FIG. 3. Alternatively, magnet 76 and transfer mechanism 38 may be moved in unison to retain target bound solid phase substrate 54 on first region 46 of lower surface 44 of upper plate 40 of transfer mechanism 38 to receptacle 58. Further, it is noted that cylindrical sidewall 48 acts to adequately space target bound solid phase substrate 54 from inner surface 64 of receptacle 58 to prevent smearing, leaking or other loss at the interface thereof.

Transfer mechanism 38 is moved to a position wherein retention well 52 thereof is axially aligned with opening 72 in open end 62 of receptacle 58, FIG. 2. Transfer mechanism 38 is then urged by a user into open end 62 of receptacle 58 such that outer surface 80 of cylindrical sidewall 48 of transfer mechanism 38 engages inner surface 64 of receptacle 58 in a mating relationship and such that portion 82 of lower surface 44 of upper plate 40 of transfer mechanism 38 which extends radially outwardly of cylindrical sidewall 48 engages upper edge 70 of receptacle 58 so as to isolate the interior of chamber 66 of receptacle 58 from the external environment, FIG. 3. It can be appreciated that cylindrical wall 48 acts to align transfer mechanism 38 with respect to opening 72 in open end 62 of receptacle 58.

If present, magnet 76 may be moved to the second position prior to or after transfer mechanism 38 is interconnected to receptacle 58, as heretofore described. With magnet 76 in the second position, magnet 76 no longer magnetically attracts target bound solid phase substrate 54, thereby allowing target bound solid phase substrate 54 to disengage from first region 46 of transfer mechanism 38. As a result, target bound solid phase substrate 54 is free to disengage from first region 46 of transfer mechanism 38 and fall into the second fluid provided in chamber 66 of receptacle 58. To facilitate disengagement of target bound solid phase substrate 54 from first region 46 of transfer mechanism 38, it is contemplated to flick, centrifuge or magnetically attract target bound solid phase substrate 54 into receptacle 58 in order to deposit target bound solid phase substrate 54 within second fluid 69 in chamber 66 of receptacle 58.

Figure 4:
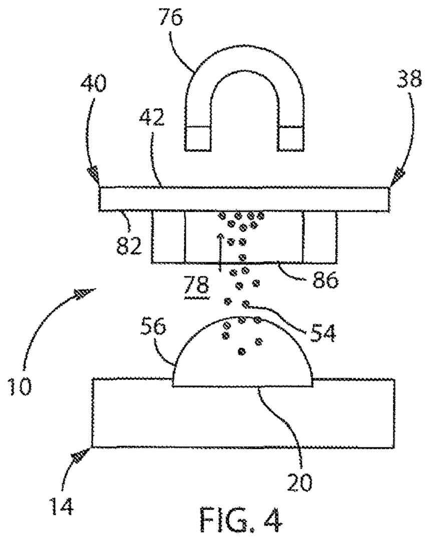
FIG. 4 a schematic, cross-sectional view of a first portion of a first alternate embodiment of a device in accordance with the present invention.
Figure 5:
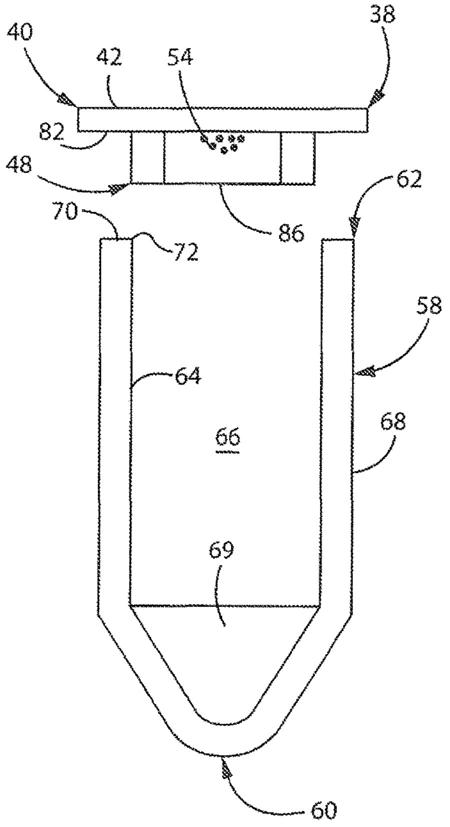
FIG. 5 an exploded, schematic, cross-sectional view of a second portion of the device of FIG. 4.
Figure 6:
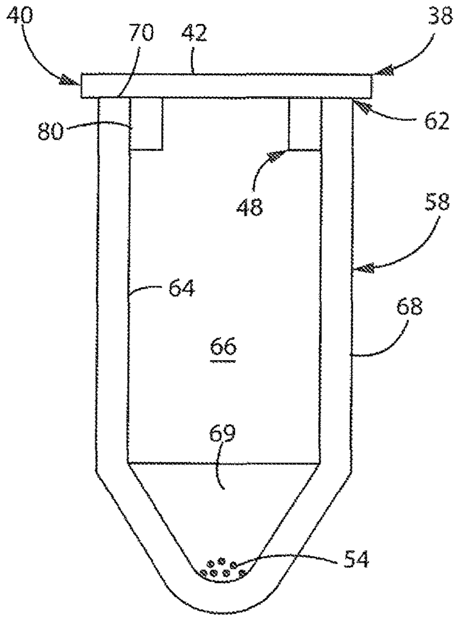
FIG. 6 is a schematic, cross-sectional view of the second portion of the device of FIG. 4.

Referring to FIGS. 4-6, it is contemplated to fill retention well 52 with selected fluid 86, e.g. a fluid intended to wash target bound solid phase substrate 54 prior to deposit in the second fluid in chamber 66 of receptacle 58. More specifically, transfer mechanism 38 is positioned such that retention well 52 is axially aligned with first region 20 of lower plate 14, and hence, with drop 56. Fluid 86 may be spaced from drop 56 by air gap 78 or in engagement with air gap 78 without deviating from the scope of the present intention. Magnet 76 is moved to the first position such that magnet 76 is positioned adjacent upper surface 42 of upper plate 40 so as to magnetically attract target bound solid phase substrate 54 in drop 56. The magnetic force generated by magnet 78 draws target hound solid phase substrate 54 from drop 56 through air gap 78 into selected fluid 86 in retention well 52. Once again, any undesired (or unbound) material in drop 56 is retained therein by surface tension.

Once target bound solid phase substrate 54 is captured by transfer mechanism 38, it is contemplated that the geometric and/or the hydrophilic natures of first region 46 of lower surface 44 of upper plate 40 of transfer mechanism 38 and inner surface 50 of cylindrical all 48, coupled with the surface tension of selected fluid 86 in retention well 52, act to retain target bound solid phase substrate 54 within retention well 52 without the need for the magnetic force of magnet 76. As such, magnet 76 may be moved to the second position as transfer mechanism 38 is moved into a mating relationship with receptacle 58, as heretofore described.

With magnet 76 in the second position, magnet 76 no longer magnetically acts on target bound solid phase substrate 54, thereby allowing target bound solid phase substrate 54 to disengage from retention well 52 of transfer mechanism 38 and be transferred into chamber 66 of receptacle 58. To facilitate disengagement of target bound solid phase substrate 54 from retention well 52 of transfer mechanism 38, it is contemplated to flick centrifuge, or magnetically attract target bound solid phase substrate 54 into receptacle 58, thereby urging target bound solid phase substrate 54 (and selected fluid 86) into second fluid 69 in chamber 66 of receptacle 58.

Figure 7:
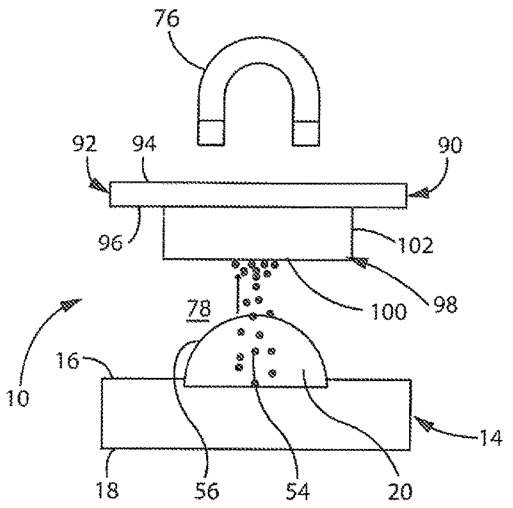
FIG. 7 a schematic, cross-sectional view of a first portion of a second alternate embodiment of a device in accordance with the present invention.
Figure 8:
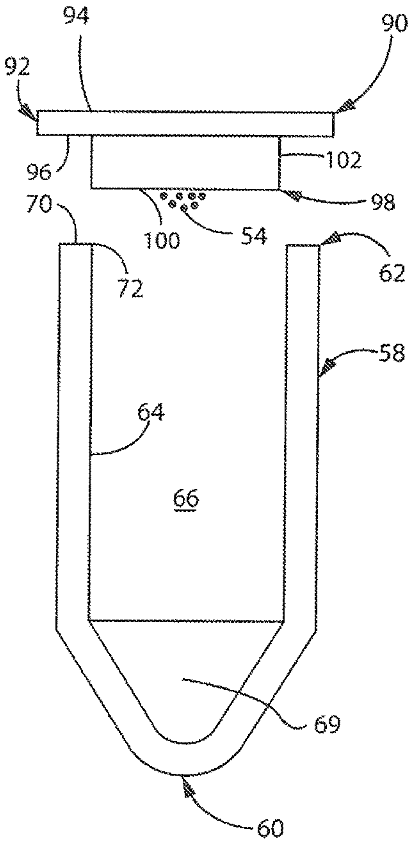
FIG. 8 an exploded, schematic, cross-sectional view of a second portion of the device of FIG. 7.
Figure 9:
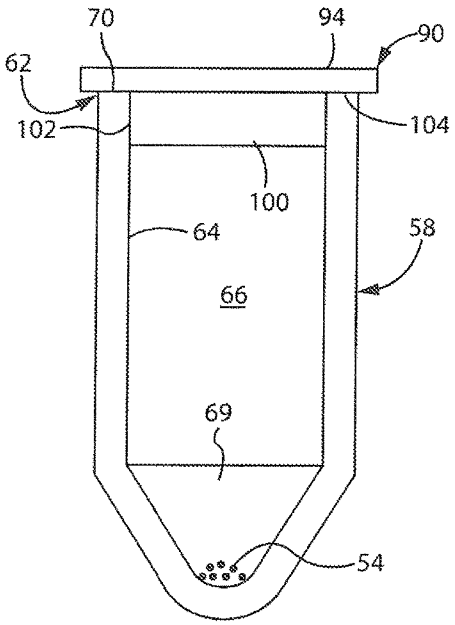
FIG. 9 is a schematic, cross-sectional view of the second portion of the device of FIG. 7.

Referring to FIGS. 7-9, an alternate transfer mechanism for use in connection with device 10 is generally designated by the reference numeral 90. Transfer mechanism 90 includes upper plate 92 having upper and lower surfaces 94 and 96, respectively. Cylinder 98 depends from lower surface 96 of upper plate 92 and terminates at an end surface 100 which lies in a plane generally parallel to lower surface 96. End surface 100 may hydrophilic and is adapted for receiving target bound solid phase substrate 54 thereon.

In operation, transfer mechanism 90 is positioned such that cylinder 98, and hence end surface 100, is axially aligned with first region 20 of lower plate 14, and hence, with drop 56. End surface 100 of cylinder 98 may be spaced from drop 56 by air gap 78 or in engagement with air gap 78 without deviating from the scope of the present intention. Magnet 76 is positioned adjacent upper surface 94 of upper plate 92. It is contemplated for magnet 76 to be axially movable between a first position wherein magnet 76 is adjacent to upper surface 94 of upper plate 92 and a second position wherein magnet 76 is axially spaced from upper surface 94 of upper plate 92, for reasons hereinafter described. With magnet 76 in the first position, as heretofore described, magnet 76 magnetically attracts target bound solid phase substrate 54 in drop 56 and draws target bound solid phase substrate 54 toward end surface 100 of transfer mechanism 90. More specifically, the magnetic force generated by magnet 76 draws target bound solid phase substrate 54 from drop 56 through air gap 78 to end surface 100. Any undesired (or unbound) material in drop 56 is retained therein by surface tension.

Once target bound solid phase substrate 54 is captured by transfer mechanism 90, it is contemplated that the geometric and/or the hydrophilic nature of end surface 100 of cylinder 98 of transfer mechanism 90 retain target bound solid phase substrate 54 thereon without the need for the magnetic force of magnet 76. As such, magnet 76 may be moved to the second position as transfer mechanism 90 is moved into a mating relationship with receptacle 58. Alternatively, magnet 76 and transfer mechanism 90 may be moved in unison to retain target bound solid phase substrate 54 on end surface 100 of transfer mechanism 90 as transfer mechanism 90 is moved to receptacle 58.

Transfer mechanism 90 is moved to a position wherein cylinder 98 thereof is axially aligned with opening 72 in open end 62 of receptacle 58, FIG. 8. Transfer mechanism 90 is then urged by a user into open end 62 of receptacle 58 such that outer surface 102 of cylinder 98 of transfer mechanism 90 engages inner surface 64 of receptacle 58 in a mating relationship and such that portion 104 of lower surface 96 of upper plate 92 of transfer mechanism 90 which extends radially outwardly of cylinder 98 engages upper edge 70 of receptacle 58 so as to isolate the interior of chamber 66 of receptacle 58 from the external environment, FIG. 9. It can be appreciated that cylinder 98 acts to align transfer mechanism 90 with respect to opening 72 in open end 62 of receptacle 58.

If present, magnet 76 may be moved to the second position prior to or after transfer mechanism 90 is interconnected to receptacle 58, as heretofore described. With magnet 76 in the second position, magnet 76 no longer magnetically attracts target bound solid phase substrate 54, thereby allowing target bound solid phase substrate 54 to disengage from end surface 100 of transfer mechanism 90. As a result, target bound solid phase substrate 54 is free to disengage from end surface 100 of transfer mechanism 90 and fall into second fluid 69 provided in chamber 66 of receptacle 58. To facilitate disengagement of target bound solid phase substrate 54 from end surface 100 of transfer mechanism 90, it is contemplated to flick or centrifuge receptacle 58, thereby depositing target bound solid phase substrate 54 within second fluid 69 in chamber 66 of receptacle 58.

Figure 10:
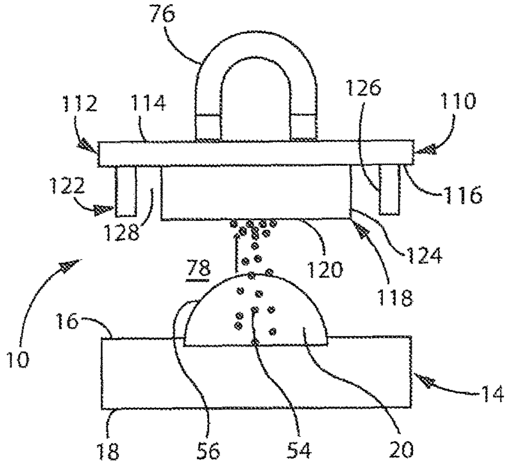
FIG. 10 a schematic, cross-sectional view of a first portion of a third alternate embodiment of a device in accordance with the present invention.
Figure 11:
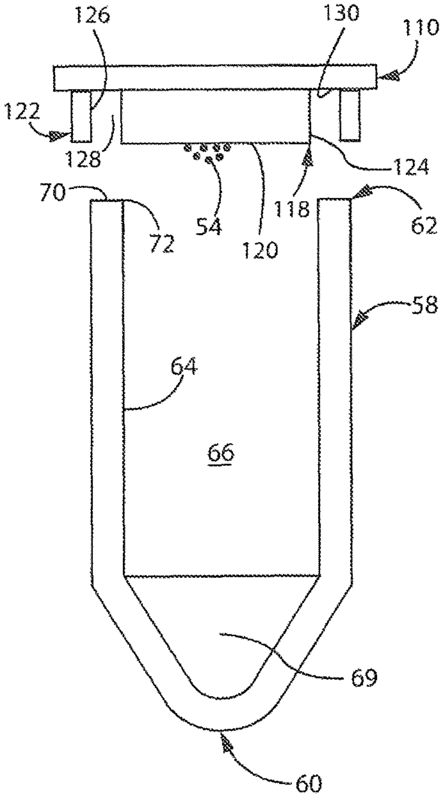
FIG. 11 an exploded, schematic, cross-sectional view of a second portion of the device of FIG. 10.
Figure 12:
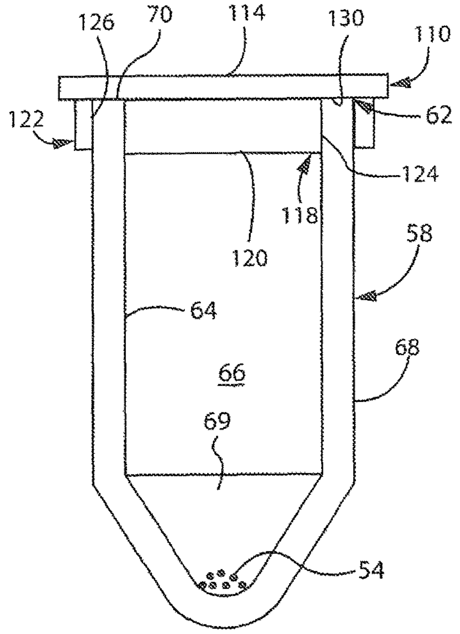
FIG. 12 is a schematic, cross-sectional view of the second portion of the device of FIG. 10.
Figure 13:
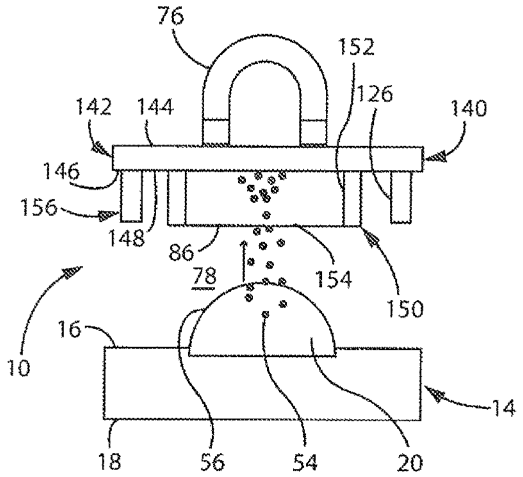
FIG. 13 a schematic, cross-sectional view of a first portion of a fourth alternate embodiment of a device in accordance with the present invention.

Referring to FIGS. 10-12, an alternate transfer mechanism for use in connection with device 10 is generally designated by the reference numeral 110. Transfer mechanism 110 includes upper plate 112 having upper and lower surfaces 114 and 116, respectively. Cylinder 118 depends from lower surface 116 of upper plate 112 and terminates at an end surface 120 which lies in a plane generally parallel to lower surface 116. End surface 120 is hydrophilic and is adapted for receiving target bound solid phase substrate 54 thereon. Transfer mechanism 110 further generally cylindrical sidewall 122 depending from lower surface 116 of upper plate 112. Sidewall 122 includes inner surface 126 which is radially spaced from outer surface 124 of cylinder 118 by a distance generally equal to the radial thickness of upper edge 70 of receptacle 58. Inner surface 126 of sidewall 122 and outer surface 124 of cylinder 118 define a cavity 128 for receiving open end 62 of receptacle 58, as hereinafter described.

In operation, transfer mechanism 110 is positioned such that cylinder 118, and hence end surface 120, is axially aligned with region 20 of lower plate 14, and hence, with drop 56. End surface 120 of cylinder 118 may be spaced from drop 56 by air gap 78 or in engagement with air gap 78 without deviating from the scope of the present intention. Magnet 76 is positioned adjacent upper surface 114 of upper plate 112. It is contemplated for magnet 76 to be axially movable between a first position wherein magnet 76 is adjacent to upper surface 114 of upper plate 112 and a second position wherein magnet 76 is axially spaced from upper surface 114 of upper plate 112, for reasons hereinafter described. With magnet 76 in the first position, as heretofore described, magnet 76 magnetically attracts target bound solid phase substrate 54 in drop 56 and draws target bound solid phase substrate 54 toward end surface 120 of transfer mechanism 110. More specifically, the magnetic force generated by magnet 76 draws target bound solid phase substrate 54 from drop 56 through air gap 78 to end surface 120. Any undesired (or unbound) material in drop 56 is retained therein by surface tension.

Once target hound solid phase substrate 54 is captured by transfer mechanism 110, it is contemplated that the geometric and/or the hydrophilic nature of end surface 120 of cylinder 118 of transfer mechanism 110 retain target bound solid phase substrate 54 thereon without the need for the magnetic force of magnet 76. As such, magnet 76 may be moved to the second position as transfer mechanism 110 is moved into a mating relationship with receptacle 58. Alternatively, magnet 76 and transfer mechanism 110 may be moved in unison to retain target bound solid phase substrate 54 on end surface 120 of transfer mechanism 110 as transfer mechanism 110 is moved to receptacle 58.

Transfer mechanism 110 is moved to a position wherein cylinder 118 thereof is axially aligned with opening 72 in open end 62 of receptacle 58, FIG. 11. Transfer mechanism 110 is then urged by a user toward open end 62 of receptacle 58 such that outer surface 124 of cylinder 118 of transfer mechanism 110 engages inner surface 64 of receptacle 58 in a mating relationship and such that open end 62 of receptacle 58 is received in cavity 128, FIG. 12. In addition, with open end 62 of receptacle 58 received in cavity 128, outer surface 68 of receptacle 58 engages inner surface 126 of sidewall 122 and portion 130 of lower surface 116 of upper plate 112 of transfer mechanism 110 which extends between outer surface 124 of cylinder 118 and inner surface 126 of sidewall 122 engages upper edge 70 of receptacle 58. As described, transfer mechanism 110 interconnected to receptacle 58, the interior of chamber 66 of receptacle 58 is isolated from the external environment. It can be appreciated that cylinder 118 and sidewall 122 act to align transfer mechanism 110 with respect to opening 72 in open end. 62 of receptacle 58.

If present, magnet 76 may be moved to the second position prior to or after transfer mechanism 110 is interconnected to receptacle 58, as heretofore described. With magnet 76 in the second position, magnet 76 no longer magnetically attracts target bound solid phase substrate 54, thereby allowing target bound solid phase substrate 54 to disengage from end surface 120 of transfer mechanism 110 fall into the second fluid provided in chamber 66 of receptacle 58. To facilitate disengagement of target bound solid phase substrate 54 from end surface 120 of transfer mechanism 110, it is contemplated to flick or centrifuge receptacle 58, thereby depositing target bound solid phase substrate 54 within second fluid 69 in chamber 66 of receptacle 58.

Referring to FIGS. 13-16, a still further embodiment of a transfer mechanism for use with device 10 is generally designated by the reference number 140. Transfer mechanism 140 includes upper plate 142 having upper and lower surfaces 144 and 146, respectively. Except as hereinafter described, lower surface 146 of upper plate 142 is hydrophobic. Lower surface 146 of upper plate 142 includes first region 148 defined by generally cylindrical inner sidewall 150 depending from lower surface 146 of upper plate 142 such that first region 148 has a generally circular configuration. As described, inner surface 152 of cylindrical inner sidewall 150 defines retention well 154, for reasons hereinafter described. It can be appreciated that other configurations of first region 148, cylindrical inner sidewall 150 and retention well 154 are contemplated as being within the scope of the present invention. It is intended for a selected fluid to retained on first region 148 and within retention well 154, as hereinafter described. As such, it is contemplated for first region 148 to be hydrophilic. It is further contemplated for inner surface 152 to be hydrophilic so as to facilitate the retention of the selected fluid in retention well 154.

Transfer mechanism 140 further includes generally cylindrical outer sidewall 156 depending from lower surface 146 of upper plate 142. Outer sidewall 156 includes inner surface 158 which is radially spaced from outer surface 160 of inner sidewall 150 by a distance generally equal to the radial thickness of upper edge 70 of receptacle 58. Inner surface 158 of outer sidewall 156 and outer surface 160 of inner sidewall 150 define a cavity 162 for receiving open end 62 of receptacle 58, as hereinafter described.

In operation, retention well 154 of transfer mechanism 140 with selected fluid 86, e.g. a fluid intended to wash target bound solid phase substrate 54 prior to deposit in the second fluid in chamber 66 of receptacle 58. More specifically, transfer mechanism 140 is positioned such that retention well 154 is axially aligned with first region 20 of lower plate 14, and hence, with drop 56. Fluid 86 may be spaced from drop 56 by air gap 78 or in engagement with air gap 78 without deviating from the scope of the present intention. Magnet 76 is moved to the first position such that magnet 76 is positioned adjacent upper surface 144 of upper plate 142 so as to magnetically attract target bound solid phase substrate 54 in drop 56. The magnetic force generated by magnet 76 draws target bound solid phase substrate 54 from drop 56 through air gap 78 into selected fluid 86 in retention well 154. Once again, any undesired (or unbound) material in drop 56 is retained therein by surface tension.

Once target bound solid phase substrate 54 is captured by transfer mechanism 140, it is contemplated that the hydrophilic natures of first region 148 of lower surface 146 of upper plate 142 of transfer mechanism 140 and inner surface 152 of inner sidewall 150, coupled with the surface tension of selected fluid 86 in retention well 154, act to retain target bound solid phase substrate 54 within retention well 154 without the need for the magnetic force of magnet 76. As such, magnet 76 may be moved to the second position as transfer mechanism 140 is moved into a mating relationship with receptacle 58, as hereinafter described.

Figure 14:
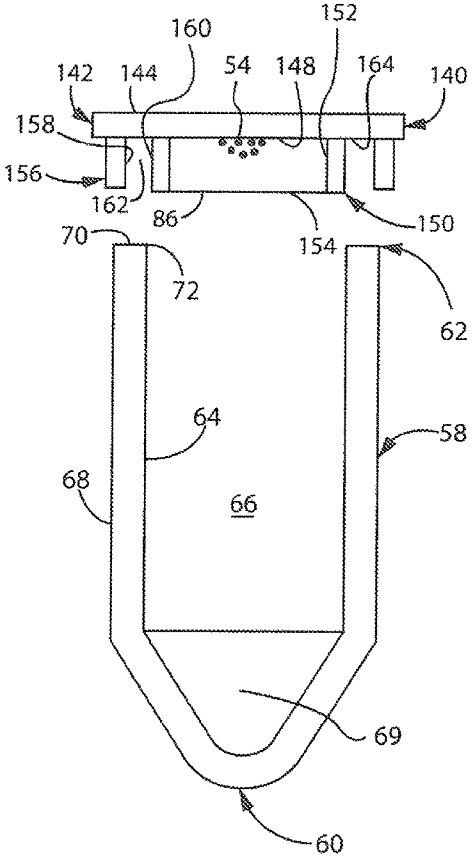
FIG. 14 an exploded, schematic, cross-sectional view of a second portion of the device of FIG. 13.
Figure 15:
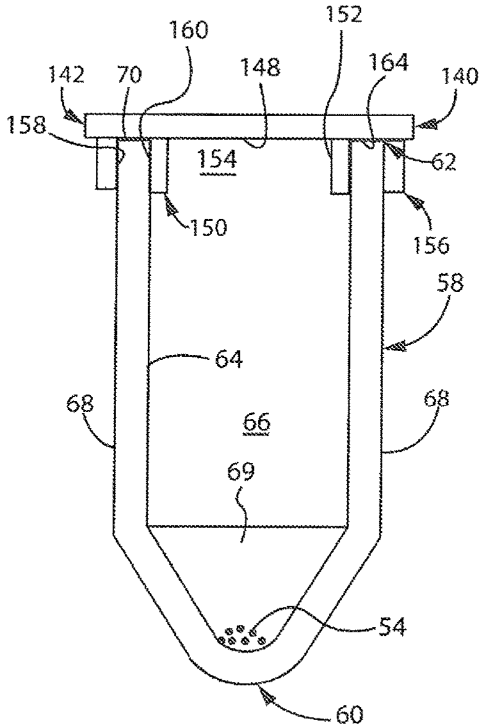
FIG. 15 is a schematic, cross-sectional view of the second portion of the device of FIG. 13.

Transfer mechanism 140 is moved to a position wherein retention well 154 thereof is axially aligned with opening 72 in open end 62 of receptacle 58, FIG. 14. Transfer mechanism 140 is then urged by a user into open end 62 of receptacle 58 such that outer surface 160 of inner sidewall 150 of transfer mechanism 140 engages inner surface 64 of receptacle 58 in a mating relationship and such that open end 62 of receptacle 58 is received in cavity 162, FIG. 15. More specifically, with open end 62 of receptacle 58 is received in cavity 162, outer surface 68 of receptacle 58 engages inner surface 158 of outer sidewall 156 and portion 164 of lower surface 146 of upper plate 142 of transfer mechanism 140 which extends between outer surface 160 of inner sidewall 150 and inner surface 158 of outer sidewall 156 engages upper edge 70 of receptacle 58. As described, with transfer mechanism 140 interconnected to receptacle 58, the interior of chamber 66 of receptacle 58 is isolated from the external environment. It can be appreciated that inner and outer sidewalls 150 and 156, respectively, of transfer mechanism 140 act to align transfer mechanism 110 with respect to opening 72 in open end 62 of receptacle 58.

With magnet 76 in the second position, magnet 76 no longer magnetically acts on target bound solid phase substrate 54, thereby allowing target bound solid phase substrate 54 to disengage from retention well 154 of transfer mechanism 140 and be transferred into chamber 66 of receptacle 58. To facilitate disengagement of target bound solid phase substrate 54 from retention well 154 of transfer mechanism 140, it is contemplated to flick or centrifuge receptacle 58, thereby urging target bound solid phase substrate 54 (and selected fluid 86) into second fluid 69 in chamber 66 of receptacle 58.

Figure 16:
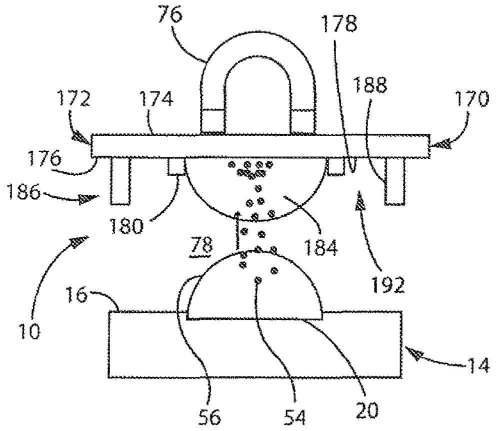
FIG. 16 a schematic, cross-sectional view of a first portion of a fifth alternate embodiment of a device in accordance with the present invention.
Figure 17:
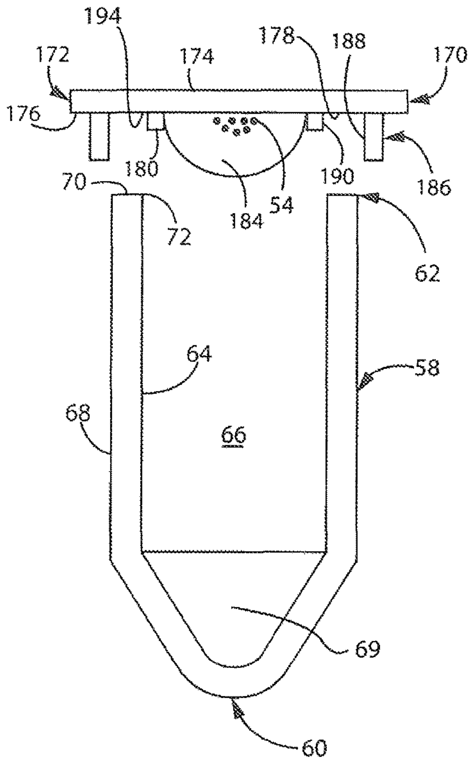
FIG. 17 an exploded, schematic, cross-sectional view of a second portion of the device of FIG. 16.
Figure 18:
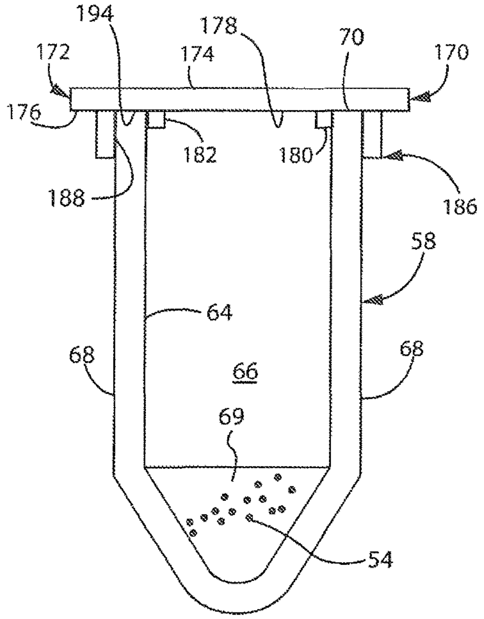
FIG. 18 is a schematic, cross-sectional view of the second portion of the device of FIG. 16.

Referring to FIGS. 16-18, a still further embodiment of a transfer mechanism for use with device 10 is generally designated by the reference number 170. Transfer mechanism 170 includes upper plate 172 having upper and lower surfaces 174 and 176, respectively. Except as hereinafter described, lower surface 176 of upper plate 172 is hydrophobic. Lower surface 176 of upper plate 172 includes first region 178 defined by generally circular pinning member 180 extending about the outer periphery thereof and depending from lower surface 176 of upper plate 172 such that first region 178 has a generally circular configuration. As described, inner edge 182 of pinning member 180 is adapted to receive second drop 184 of selected fluid, for reasons hereinafter described. It can be appreciated that other configurations of first region 178 and pinning member 180 are contemplated as being within the scope of the present invention. It is contemplated for first region 178 to be hydrophilic so as to facilitate retention of the selected fluid thereon.

Transfer mechanism 170 further includes generally cylindrical outer sidewall 186 depending from lower surface 176 of upper plate 172. Outer sidewall 186 includes inner surface 188 which is radially spaced from outer edge 190 of pinning member 180 by a distance generally equal to the radial thickness of upper edge 70 of receptacle 58. Inner surface 188 of outer sidewall 186 and outer edge 190 of pinning member 180 define a cavity 192 for receiving open end 62 of receptacle 58, as hereinafter described.

In operation, drop 184 of selected fluid, e.g. a fluid intended to wash target bound solid phase substrate 54 prior to deposit into receptacle 58, is deposited on first region 178 and pinned thereon by inner edge 182 of pinning member 180. Transfer mechanism 170 is positioned such that drop 184 is axially aligned with first region 20 of lower plate 14, and hence, with chop 56. Second drop 184 may be spaced from drop 56 by air gap 78 or in engagement with air gap 78 with deviating from the scope of the present intention. Magnet 76 is moved to the first position such that magnet 76 is positioned adjacent upper surface 174 of upper plate 172 so as to magnetically attract target bound solid phase substrate 54 in drop 56. The magnetic force generated by magnet 76 draws target bound solid phase substrate 54 from drop 56 through air gap 78 into drop 184 of the selected fluid. Once again, any undesired (or unbound) material in drop 56 is retained therein by surface tension.

Once target bound solid phase substrate 54 is captured by transfer mechanism 170, it is contemplated that the hydrophilic natures of first region 178 of lower surface 176 of upper plate 172 of transfer mechanism 170 and inner edge 182 of pinning member 180, coupled with the surface tension of selected drop 184, act to retain target bound solid phase substrate 54 within drop 184 without the need for the magnetic force of magnet 76. As such, magnet 76 may be moved to the second position as transfer mechanism 170 is moved into a mating relationship with receptacle 58, as hereinafter described.

Transfer mechanism 170 is moved to a position wherein drop 184 is axially aligned with opening 72 in open end 62 of receptacle 58, FIG. 17. Transfer mechanism 170 is then urged by a user into open end 62 of receptacle 58 such that outer edge 190 of pinning member 180 of transfer mechanism 170 engages inner surface 64 of receptacle 58 in a mating relationship and such that open end 62 of receptacle 58 is received in cavity 192, FIG. 18. More specifically, with open end 62 of receptacle 58 is received in cavity 192, outer surface 68 of receptacle 58 engages inner surface 188 of outer sidewall 186 and portion 194 of lower surface 176 of upper plate 172 of transfer mechanism 170 which extends between outer edge 190 of pinning member 180 and inner surface 188 of outer sidewall 186 engages upper edge 70 of receptacle 58. As described, with transfer mechanism 170 interconnected to receptacle 58, the interior of chamber 66 of receptacle 58 is isolated from the external environment. It can be appreciated that pinning member 180 and outer sidewall 186 of transfer mechanism 170 act to align transfer mechanism 170 with respect to opening 72 in open end 62 of receptacle 58.

With magnet 76 in the second position, magnet 76 no longer magnetically acts on target bound solid phase substrate 54, thereby allowing target bound solid phase substrate 54 and drop 184 to be transferred into chamber 66 of receptacle 58. To facilitate disengagement of target bound solid phase substrate 54 and drop 184 from transfer mechanism 170, it is contemplated to flick or centrifuge receptacle 58, thereby urging target bound solid phase substrate 54 and drop 184 into second fluid 69 in chamber 66 of receptacle 58.

Figure 19:
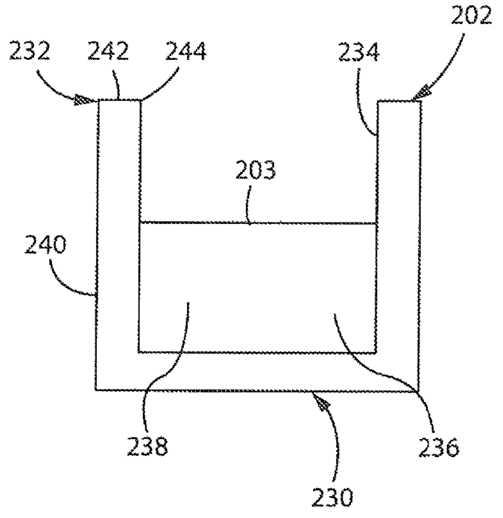
FIG. 19 is a schematic, cross-sectional view of a first embodiment of a sample container for use in conjunction with the device of the present invention.
Figure 20:
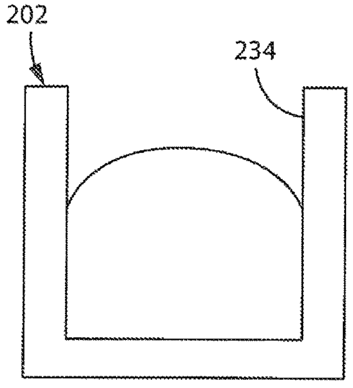
FIG. 20 is a schematic, cross-sectional view of a second embodiment of a sample container for use in conjunction with the device of the present invention.

As heretofore described, in order to effectuate the transfer of target bound solid phase substrate 54 from a first fluid to a second fluid with the various transfer mechanisms heretofore described, it is necessary for the first fluid containing the target bound solid phase substrate 54 to have a non-concave-shaped meniscus (e.g. drop 56) such that target bound solid phase substrate 54 cluster at the apex of fluid prior to being magnetically drawn from the first fluid to the corresponding transfer mechanisms heretofore described. However, it can be appreciated that the first fluid received in sample container 202 (e.g. a test tube or a well of a microfluidic device or a well plate) will have a concave or flat upper surface 203, FIG. 19. Hence, in order to effectuate the methodology heretofore described, it is necessary to alter the shape of the upper surface of the first fluid in the sample container to have a non-concave-shaped meniscus similar to drop 56. In order to alter the shape of the upper surface of the first fluid in sample container 202, various alternatives are possible. By way of example, by overfilling the first fluid in sample container 202, the upper surface of the first fluid will have a non-concave-shaped meniscus. Alternatively, it is contemplated for inner surface 234 of sample container 202 to by hydrophobic, FIG. 20. By providing a hydrophobic inner surface 234, the first fluid provided in sample container 202 will have a non-concave-shaped meniscus.

Figures 29A, 29B:
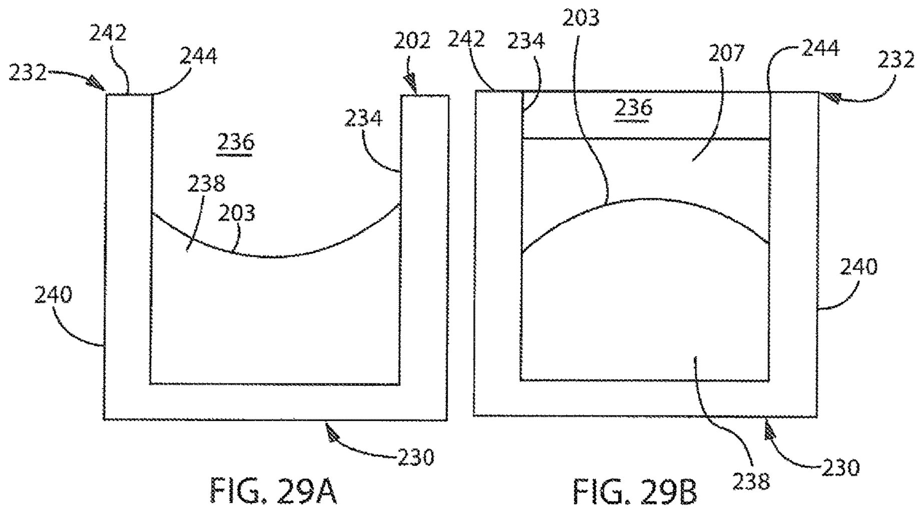
FIG. 29*a* is a schematic, cross-sectional view of a fourth embodiment of a sample container for use in conjunction with the device of the present invention.
FIG. 29*b* is a schematic, cross-sectional view of the fourth embodiment of the sample container of FIG. 29*a* in operation.

Referring to FIGS. 29*a*-29*b*, in circumstances wherein first fluid 238 received in sample container 202 has a concave upper surface 203, it is contemplated to deposit an immiscible fluid 207 on upper surface 203 of first fluid 238. As a result, the interfacial energy between first fluid 238 and immiscible fluid 207 causes a reversal in the shape of first fluid 238 such that the upper surface 203 of first fluid 238 is convex.

Figures 30A, 30B:
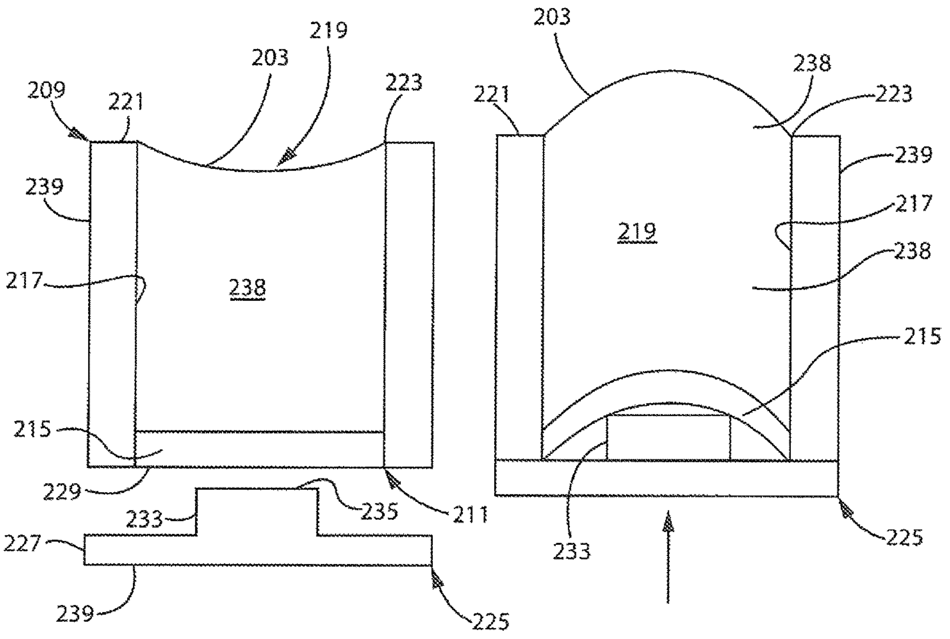
FIG. 30*a* an exploded, schematic, cross-sectional view of a fifth embodiment of a sample container for use in conjunction with the device of the present invention.
FIG. 30*b* is a schematic, cross-sectional view of the fifth embodiment of a sample container in operation.

Referring to FIGS. 30*a*-30*b*, an alternate embodiment of a sample container is generally designated by the reference numeral 209. Sample container 209 includes a lower open end 211 and an upper open end 213. Lower open end 211 of sample container 209 is closed by a flexible membrane 215. Cylindrical inner surface 217 of sample container 209 defines chamber 219 for receiving first fluid 238 therein. Sample container 209 is further defined by outer surface 239 and by upper edge 221, which extends between inner and outer surfaces 217 and 239, respectively, and which defines opening 223 in open end 213. Opening 223 allows for fluid communication between the interior of chamber 219 of sample container 209 and the various transfer mechanisms heretofore described.

Actuation element 225 includes lower plate 227 having upper and lower surfaces 229 and 231, respectively. Cylinder 233 extends upwardly from upper surface 229 of lower plate 227 and terminates at an end surface 235 which lies in a plane generally parallel to upper surface 229. End surface 235 is adapted for engaging flexible membrane 215, as hereinafter described.

In operation, chamber 219 in sample container 209 is filled with first fluid 238 such that first fluid 238 has a concave upper surface 203. Actuation element 225 is aligned with lower open end 211 of sample container 209 and urged upwardly, FIG. 30*b*, such that end surface 235 of cylinder 233 engages flexible member 215 and such the outer peripheral portion of upper surface 229 of actuation element 225 overlaps lower open end 211 of sample container 209. End surface 235 of cylinder 233 urges flexible member 215 into chamber 219 of sample container 209 so as to cause a reversal in the shape of first fluid 238 such that the upper surface 203 of first fluid 238 is convex.

Figure 21:
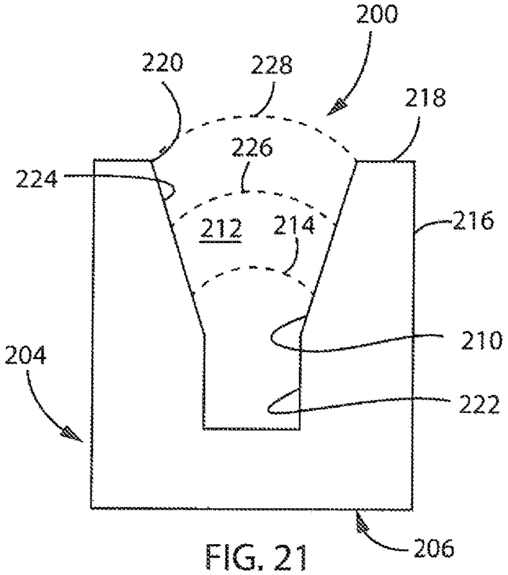
FIG. 21 is a schematic, cross-sectional view of a third embodiment of a sample container for use in conjunction with the device of the present invention.

Referring to FIG. 21, a further alternate sample container, generally designated by the reference number 204, may be used to provide the first fluid contained therein with a non-concave-shaped meniscus. Sample container 204 includes a first closed end 206 and second open end 208. Inner surface 210 of sample container 204 defines chamber 212 for receiving first fluid 214 therein. Sample container 204 is further defined by outer surface 216 and by upper edge 218, which extends between inner and outer surfaces 210 and 216, respectively, and which defines opening 220 in open end 208. Opening 220 allows for fluid communication between the interior of chamber 212 of sample container 204 and the various transfer mechanism heretofore described. In order to generate a non-concave-shaped meniscus from first fluid 214 in chamber 212 of sample container 204, inner surface 210 is provided with a generally cylindrical lower portion 222 and a beveled portion 224 extending between lower portion 222 of inner surface 210 and upper edge 218 of sample container 204. It is understood that beveled portion 224 enables first fluid 214 to have a non-concave-shaped meniscus and, as depicted by dotted lines 226 and 228, and to maintain, the non-concave-shaped meniscus regardless of volume of first fluid 214 in beveled portion 224 partially defining chamber 212 in sample container 204.

If is further contemplated to provide an adaptor within sample container 202 which fabricates a non-concave-shaped meniscus from the first fluid provided therein. Referring back to FIG. 19, in the depicted embodiment, sample container 202 includes a first closed end 230 and second open end 232. Cylindrical inner surface 234 of sample container 202 defines chamber 236 for receiving first fluid 238 therein. Sample container 202 is further defined by outer surface 240 and by upper edge 242, which extends between inner and outer surfaces 234 and 240, respectively, and which defines opening 244 in open end 232. Opening 244 allows for fluid communication between the interior of chamber 236 of sample container 202 and the various transfer mechanisms heretofore described.

Figure 22A:
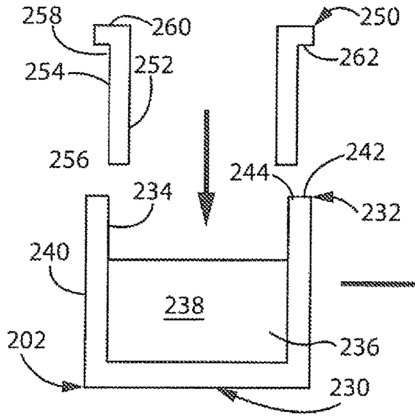
FIG. 22*a* is an exploded, schematic, cross-sectional view of a first embodiment of an adaptor receivable within the sample container of FIG. 19.
Figure 22B:
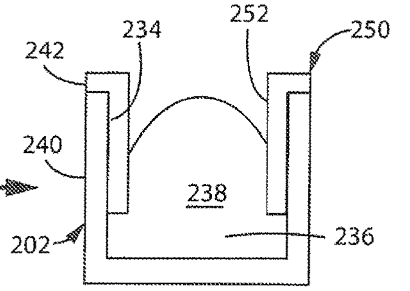
FIG. 22*b* is a schematic, cross-sectional view of the first embodiment of the adaptor of FIG. 22*a* received within the sample container of FIG. 19.

Referring to FIGS. 22*a*-22*b*, a first embodiment of an adapter for generating a non-concave-shaped meniscus from first fluid 238 provided within chamber 236 of sample container 202 is generally designated by the reference number 250. Adapter 250 is generally tubular and is defined by a generally hydrophobic inner surface 252 and an outer surface 254. Adaptor 250 has an outer diameter generally equal to the diameter of chamber 236 of sample container 202. Adapter 250 further includes lower edge 256 and upper edge 258 having lip 260 extending radially outward therefrom. Lip 260 includes a lower surface 262 adapted for engagement with upper edge 242 of sample container 202.

In operation, adaptor 250 is inserted into opening 244 in open end 232 of sample container 202 such that outer surface 254 of adaptor 250 forms a mating relationship with inner surface 234 of sample container 202 so as to prevent first fluid 238 from flowing therebetween and such that lower surface 262 of lip 260 engages upper edge 242 of sample container 202, FIG. 22*b*. With adaptor 250 positioned as described, the hydrophobic nature of inner surface 252 of adaptor 250 causes first fluid 238 provided in chamber 236 of sample container 202 to have a non-concave-shaped meniscus. The non-concave-shaped meniscus of first fluid 238 in chamber 236 of sample container 202 causes target bound solid phase substrate 54 to cluster at the apex thereof as target bound solid phase substrate 54 are magnetically drawn from first fluid 238 to a corresponding transfer mechanism, as heretofore described.

Figure 23A:
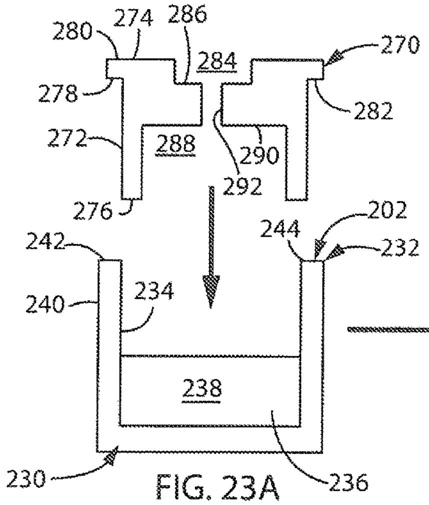
FIG. 23*a* is an exploded, schematic, cross-sectional view of a second embodiment of an adaptor receivable within the sample container of FIG. 19.
Figure 23B:
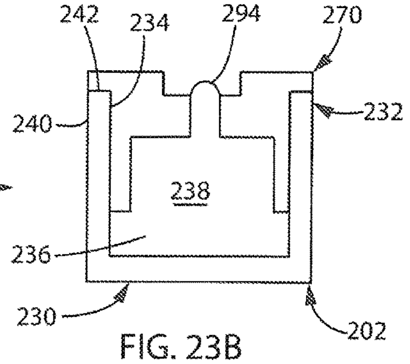
FIG. 23*b* is a schematic, cross-sectional view of the second embodiment of the adaptor of FIG. 23*a* received within the sample container of FIG. 19.

Referring to FIGS. 23*a*-23*b*, a further embodiment of an adapter for generating a non-concave-shaped meniscus from first fluid 238 provided within chamber 236 of sample container 202 is generally designated by the reference number 270. Adapter 270 extends along an axis and is defined by a cylindrical outer surface 272, upper surface 274 and lower surface 276. Adaptor 270 has an outer diameter generally equal to the diameter of chamber 236 of sample container 202. Upper edge 278 of outer surface 274 includes lip 280 extending radially outward therefrom. Lip 280 includes a lower surface 282 adapted for engagement with upper edge 242 of sample container 202. Upper surface 274 of adaptor 270 includes recess 284 provided therein and adapted for receiving one of the transfer mechanisms heretofore described. Recess 284 is partially defined by recessed surface 286 which is generally parallel to upper surface 274 of adaptor 270. Similarly, lower surface 276 of adaptor 270 includes recess 288 provided therein. Recess 288 is partially defined by recessed surface 290 which is generally parallel to recessed surface 286 and to upper surface 274 of adaptor 270. Orifice 292 extends between recessed surface 290 and recessed surface 286.

In operation, adaptor 270 is inserted into opening 244 in open end 232 of sample container 202 such that outer surface 272 of adaptor 270 forms a mating relationship with inner surface 234 of sample container 202 so as to prevent first fluid 238 from flowing therebetween and such that lower surface 282 of lip 280 engages upper edge 242 of sample container 202. FIG. 23*b*. With adaptor 270 positioned as described, adapter 270 displaces first fluid 238 in chamber 236 of sample container 202 such that first fluid 238 flows through orifice 292 and forms drop 294 having a non-concave-shaped meniscus. The non-concave-shaped meniscus of drop 294 causes target bound solid phase substrate 54 to cluster at the apex thereof as target bound solid phase substrate 54 are magnetically drawn from first fluid 238 (and hence, drop 294) to a corresponding transfer mechanism, as heretofore described.

Figure 24:
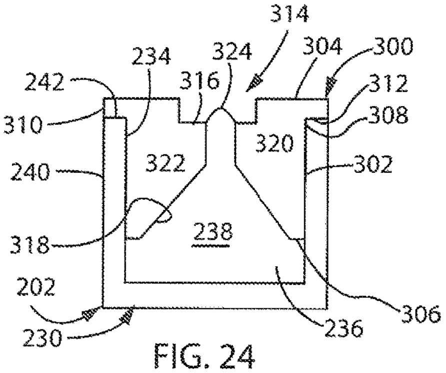
FIG. 24 is a schematic, cross-sectional view of a third embodiment of the adaptor received within the sample container of FIG. 19.

Referring to FIG. 24, a still further embodiment of an adapter for generating a non-concave-shaped meniscus from first fluid 238 provided within chamber 236 of sample container 202 is generally designated by the reference number 300. Adapter 300 extends along an axis and is defined by a cylindrical outer surface 302, upper surface 304 and lower surface 306. Adaptor 300 has an outer diameter generally equal to the diameter of chamber 236 of sample container 202. Upper edge 308 of outer surface 302 includes lip 310 extending radially outward therefrom. Lip 310 includes a lower surface 312 adapted for engagement with upper edge 242 of sample container 202. Upper surface 304 of adaptor 300 includes recess 314 provided therein and adapted for receiving one of the transfer mechanisms heretofore described. Recess 314 is partially defined by recessed surface 316 which is generally parallel to upper surface 304 of adaptor 300. Similarly, lower surface 306 of adaptor 300 includes a tapered or generally conical-shaped recess 318 provided therein. Recess 318 includes an upper end 320 which communicates with recessed surface 316 by orifice 322.

In operation, adaptor 300 is inserted into opening 244 in open end 232 of sample container 202 such that outer surface 302 of adaptor 300 forms a mating relationship with inner surface 234 of sample container 202 so as to prevent first fluid 238 from flowing therebetween and such that lower surface 312 of lip 310 engages upper edge 242 of sample container 202. With adaptor 300 positioned as described, adapter 300 displaces first fluid 238 in chamber 236 of sample container 202 such that first fluid 238 flows into recess 318 and through orifice 322 to forms drop 324 having a non-concave-shaped meniscus on recessed surface 316. It is intended that the conical shape of recess 318 to prevent air bubbles or target bound solid phase substrate 54 from getting trapped under adaptor 300. The non-concave-shaped meniscus of drop 324 causes target bound solid phase substrate 54 to cluster at the apex thereof as target bound solid phase substrate 54 are magnetically drawn from first fluid 238 (and hence, drop 324) to a corresponding transfer mechanism, as heretofore described.

Figure 25A:
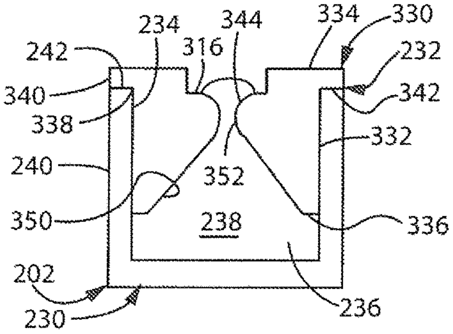
FIG. 25*a* is a schematic, cross-sectional view of a fourth embodiment of the adaptor received within the sample container of FIG. 19.
Figure 25B:
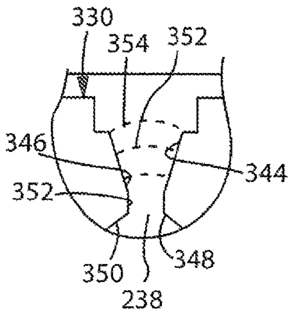
FIG. 25*b* is an enlarged, schematic, cross-sectional view showing a portion of the adaptor of FIG. 25*a;*

Referring to FIGS. 25*a*-25*b*, a still further embodiment of an adapter for generating a non-concave-shaped meniscus from first fluid 238 provided within chamber 236 of sample container 202 is generally designated by the reference number 330. Adapter 330 extends along an axis and is defined by a cylindrical outer surface 332, upper surface 334 and lower surface 336. Adaptor 330 has an outer diameter generally equal to the diameter of chamber 236 of sample container 202. Upper edge 338 of outer surface 332 includes lip 340 extending radially outward therefrom. Lip 340 includes a lower surface 342 adapted for engagement with upper edge 242 of sample container 202. Upper surface 334 of adaptor 330 includes beveled or conical-shaped recess 344 provided therein and adapted for communicating with one of the transfer mechanisms heretofore described. Lower end 346 of recess 344 communicates with upper end 348 of a tapered or generally conical-shaped recess 350 in lower surface 336 via orifice 352 extending therebetween.

In operation, adaptor 330 is inserted into opening 244 in open end 232 of sample container 202 such that outer surface 332 of adaptor 330 forms a mating relationship with inner surface 234 of sample container 202 so as to prevent first fluid 238 from flowing therebetween and such that lower surface 342 of lip 340 engages upper edge 242 of sample container 202. With adaptor 330 positioned as described, adapter 330 displaces first fluid 238 in chamber 236 of sample container 202 such that first fluid 238 flows into recess 350, through orifice 322 and into recess 344. The conical shape of recess 344 causes first fluid 238 therein to have a non-concave-shaped meniscus. It can be appreciated that due to the conical shape of recess 344, first fluid 238 will maintains its non-concave-shaped meniscus, as depicted by dotted lines 352 and 354, over a range of volumes of first fluid 238 therein, FIG. 25*b*. Further, it is intended that the conical shape of recess 350 prevent air bubbles from getting trapped under adaptor 330. The non-concave-shaped meniscus of first fluid 238 causes target bound solid phase substrate 54 to cluster at the apex thereof as target bound solid phase substrate 54 are magnetically drawn from first fluid 238 to a corresponding transfer mechanism, as heretofore described.

Figure 26:
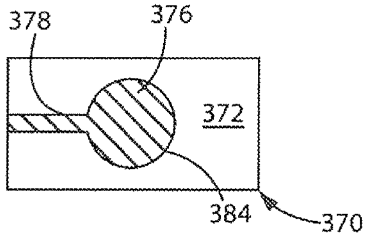
FIG. 26 is a top plan view of an intermediate fluid layer for use with the device of the present invention.
Figure 27:
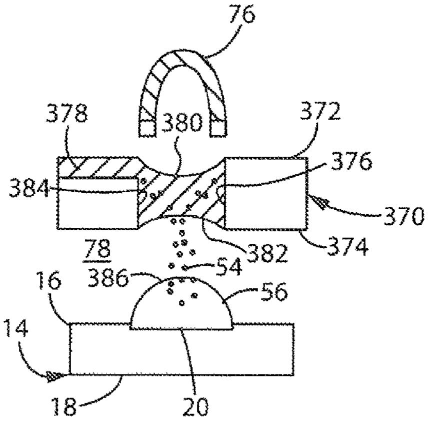
FIG. 27 is a cross-section view the intermediate fluid layer of FIG. 26 with the fluid therein in a first configuration.
Figure 28:
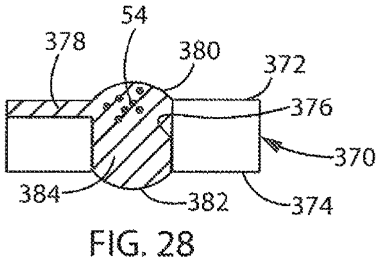
FIG. 28 is a cross-section view the intermediate fluid layer of FIG. 26 with the fluid therein in a second configuration.

Referring to FIGS. 26-28, it is further contemplated to provided an intermediate fluid layer between a convex-shaped meniscus of the first fluid (e.g. drop 56 or a drop formed from the first fluid 238 in sample container 202, as heretofore described) and a selected one of the various transfer mechanisms heretofore described (e.g. in air gap 78). More specifically, an intermediate fluid layer in accordance with the present invention is generally designated by the reference numeral 370. Layer 370 includes upper and lower surfaces 372 and 374, respectively, which are generally planar and parallel to each other. Passage 376 extends along an axis between the upper and lower surfaces 372 and 374, respectively. Channel 378 extends along upper surface 372 of layer 370 and communicates with passage 376.

In operation, it is contemplated to fill passage 376 with desired fluid 384 such as a wash or an intermediate fluid to stain or otherwise prepare the target for analysis. Initially, it is intend for upper meniscus 380 and lower meniscus 382 of fluid 384 to be generally concave. Layer 370 is positioned such that passage 376 is axially aligned with a convex-shaped meniscus 386 of the first fluid (e.g. drop 56). Magnet 76 may be used to draw target bound solid phase substrate 54 from drop 56, through air gap 78 and into fluid 384 in passage 376. As best seen in FIG. 27, concave upper meniscus 380 of first fluid 384 causes target bound solid phase substrate 54 to spread to outer peripheral edges of concave upper meniscus 380 of fluid 384 in passage 376, thereby preventing target bound solid phase substrate 54 from exiting passage 376.

In order to transfer target bound solid phase substrate 54 to one of the various transfer mechanisms heretofore described, it is necessary to convert the configuration of upper meniscus 380 of fluid 384 from concave to convex. As such, additional fluid is directed into passage 376 via channel 378 in any conventional manner, FIG. 28. As the volume of fluid 384 in passage 376 increases, the configuration of the upper meniscus change from concave to convex. Once upper meniscus 380 of fluid 384 in passage 376 of layer 370 become convex, target hound solid phase substrate 54 cluster at the apex thereof. As a result, target bound solid phase substrate 54 may be magnetically drawn from fluid 384 to a corresponding transfer mechanism, as heretofore described.

It can be appreciated that the above descriptions of devices are merely exemplary of the present invention. Various modes of carrying out the invention are contemplated as being within the scope of the following claims particularly pointing out and distinctly claiming the subject matter, which is regarded as the invention.

We claim:

1. A device for transferring a target received in a first fluid at a first location to a second location, the target being bound to a solid phase substrate to form a target bound solid phase substrate, comprising:

a transfer structure having a first surface and a second surface, the second surface defining a transfer surface including a first region for receiving the target bound solid phase substrate thereon for transfer and being movable between a first position wherein the transfer surface is axially aligned with an apex of the first fluid at the first location and spaced from the apex of the first fluid by a non-liquid air gap and a second position wherein the transfer surface is aligned with the second location which is spaced from the first location;

an alignment structure for aligning the transfer surface with respect to the second location, with the transfer surface in the second position; and a force generator adjacent the first surface of the transfer structure and being configured to generate a force, the force generator being movable with respect to the transfer surface between a non-attraction position wherein the target bound solid phase substrate is free of the force and an attraction position; wherein, with the transfer surface in the first position and the force generator in the attraction position;

wherein:

the transfer surface is spaced from the first location by a distance such that the force is sufficient to attract the target bound solid phase substrate; and the target bound solid phase substrate received in the first fluid at the first location exits the first fluid and travels through the non-liquid air gap toward the first region of the transfer surface in response to the attraction of the target bound solid phase substrate to the force.

2. The device of claim 1 further comprising a sample container at the first location for receiving the first fluid and having an inner surface, the inner surface of the sample container being hydrophobic and causing the first fluid in the sample container to have a non-concave meniscus.

3. The device of claim 1 further comprising:

a sample container at the first location for receiving the first fluid and having an inner surface; and an insert receiveable in the sample container along the inner surface thereof, the insert causing the first fluid in the sample container to have a non-concave meniscus.

4. The device of claim 1 further comprising a second fluid received in a receptacle at the second location, the receptacle having an inner surface and an upper edge.

5. The device of claim 4 wherein the alignment structure includes a plate, the transfer surface extending along a first side of the plate and overlapping the upper edge of the receptacle with the transfer surface in the second position.

6. A device for transferring a target received in a first fluid at a first location to a second location, the target being bound to a solid phase substrate to form a target bound solid phase substrate, comprising:

a transfer structure having a first surface and a transfer surface, the transfer surface including a first region for receiving the target bound solid phase substrate thereon for transfer and being movable between a first position wherein the transfer surface is axially aligned with an apex of the first fluid at the first location and spaced from the apex of the first fluid by a non-liquid air gap and a second position wherein the transfer surface is aligned with the second location which is spaced from the first location;

an alignment structure for aligning the transfer surface with respect to the second location, with the transfer surface in the second position; and a force generator adjacent to the first surface of the transfer structure and being configured to generate a force, the force generator being movable with respect to the transfer surface between a non-attraction position wherein the target bound solid phase substrate is free of the force and an attraction position wherein, with the transfer surface in the first position, the force attracts the target bound solid phase substrate received in the first fluid at the first location exits the first fluid and travels through the non-liquid air gap toward the first region of the transfer surface;

wherein:

the alignment structure includes a plate and a wall depending from the transfer surface, the wall having an inner surface defining the first region of the transfer surface and an outer surface engageable with the inner surface of the receptacle with the transfer surface in the second position; and the transfer surface extends along a first side of the plate and overlaps the upper edge of the receptacle with the transfer surface in the second position.

7. The device of claim 6 wherein:

the wall is a first wall;

the receptacle includes an outer surface; and the alignment structure further includes a second wall depending from the transfer surface, the second wall having an inner surface engageable with the outer surface of the receptacle with the transfer surface in the second position and an outer surface.

8. A device for transferring a target received in a first fluid at a first location to a second location, the target being bound to a solid phase substrate to form a target bound solid phase substrate, comprising:

a transfer structure having a first surface and a transfer surface, the transfer surface including a first region for receiving the target bound solid phase substrate thereon for transfer and being movable between a first position wherein the transfer surface is axially aligned with an apex of the first fluid at the first location and spaced from the apex of the first fluid by a non-liquid air gap and a second position wherein the transfer surface is aligned with the second location which is spaced from the first location;

an alignment structure for aligning the transfer surface with respect to the second location, with the transfer surface in the second position;

a force generator adjacent to the first surface of the transfer structure and being configured to generate a force, the force generator being movable with respect to the transfer surface between a non-attraction position wherein the target bound solid phase substrate is free of the force and an attraction position wherein, with the transfer surface in the first position, the force attract the target bound solid phase substrate such that the target bound solid phase substrate received in the first fluid at the first location exits the first fluid and travels through the non-liquid air gap toward the first region of the transfer surface:

a second fluid received in a receptacle at the second location, the receptacle having an inner surface and an upper edge; and a transfer fluid provided at the first region of the transfer surface; and wherein:

the receptacle includes an outer surface; and the alignment structure includes a wall depending from the transfer surface, the wall having an inner wall surface engageable with the outer surface of the receptacle with the transfer surface in the second position and an outer wall surface.

9. The device of claim 8 wherein the first region of the transfer surface includes a pinning element extending about the outer periphery thereof, the pinning element retaining the transfer fluid in the first region of the transfer surface.

10. The device of claim 5 wherein the plate includes an upper surface on a second side thereof, the force is adjacent the upper surface of the plate with the force in the attraction position.

11. The device of claim 4 wherein the alignment structure includes a plate and a transfer element depending from a first side thereof, the transfer element terminating at the transfer surface and having an outer surface engageable with the inner surface of the receptacle with the transfer surface in the second position.

12. The device of claim 11 wherein the first side of the plate is engageable with the upper edge of the receptacle with the transfer surface in the second position.

13. The device of claim 1 wherein the force is a magnetic force.

14. The device of claim 1 further comprising an intermediate fluid disposed between the transfer surface and the first location, the target bound solid phase substrate passing through the intermediate fluid as the target bound solid phase substrate is drawn from the first location to the first region of the transfer surface.

15. A device for transferring a target from a first fluid at a first location to a second location, the target being bound to a solid phase substrate to form target bound solid phase substrate, comprising:

means for forming a non-concave meniscus with the first fluid;

a transfer structure having a first surface and a second surface, a transfer region on the second surface of the transfer structure for receiving the target bound solid phase substrate for transfer, the transfer region movable with respect to the first fluid between a first position wherein the transfer region is axially aligned with and separated from an apex of the non-concave meniscus of the first fluid by a non-liquid air gap and a second position wherein the transfer region is aligned with the second location which is spaced from the first location;

an alignment structure for aligning the transfer region with respect to the receptacle with the transfer region in the second position;

force generator adjacent to the first surface of the transfer structure and being configured to generate a force and being movable with respect to the transfer region between a non-attraction position wherein the target bound solid phase substrate is free of the force and an attraction position; wherein, with the transfer region in the first position and the force generator in the attraction position:

the transfer surface is spaced from the first location by a distance such that the force is sufficient to attract the target bound solid phase substrate in the first fluid; and the target bound solid phase substrate exits the first fluid and travels through the non-liquid air gap toward the transfer region in response to the attraction of the target bound solid phase substrate to the force.

16. The device of claim 15 wherein the first fluid is received in a sample container and wherein the forming means includes an inner surface of the sample container being hydrophobic so as to cause the first fluid in the sample container to have the non-concave meniscus.

17. The device of claim 15 wherein the first fluid is received in a sample container having an inner surface, and wherein the forming means includes an insert receiveable in the sample container along the inner surface thereof, the insert causing the first fluid in the sample container to have a non-concave meniscus.

18. The device of claim 15 further comprising an intermediate fluid disposed between the transfer region and the first fluid, the target bound solid phase substrate passing through the intermediate fluid as the target bound solid phase substrate is drawn from the first fluid to the transfer region.

19. The device of claim 15 wherein the alignment structure includes a plate and the second location includes a receptacle having an inner surface and an upper edge, the transfer region extending along a first side of the plate and the plate overlaps the upper edge of the receptacle with the transfer region in the second position.

20. The device of claim 19 wherein the alignment structure further includes a wall depending from the transfer surface, the wall engageable with the receptacle with the transfer region in the second position.

21. The device of claim 15 further comprising a transfer fluid provided at the transfer region and a pinning element extending about the outer periphery of the transfer region, the pinning element retaining the transfer fluid in the transfer region.

* * * * *